US005672633A

United States Patent [19]
Brehm et al.

[11] Patent Number: 5,672,633
[45] Date of Patent: Sep. 30, 1997

[54] POWDERY POLYMERS CAPABLE OF ABSORBING AQUEOUS LIQUIDS, A PROCESS FOR THEIR PRODUCTION AND THEIR USE AS ABSORBENTS

[75] Inventors: Helmut Brehm, Krefeld; Hans-Georg Hartan, Kevelaer, both of Germany

[73] Assignee: Chemische Fabrik Stockhausen GmbH, Krefeld, Germany

[21] Appl. No.: 615,249

[22] PCT Filed: Sep. 21, 1994

[86] PCT No.: PCT/EP94/03153

§ 371 Date: Mar. 26, 1996

§ 102(e) Date: Mar. 26, 1996

[87] PCT Pub. No.: WO95/09014

PCT Pub. Date: Apr. 6, 1995

[30] Foreign Application Priority Data

Sep. 29, 1993 [DE] Germany .................. 43 33 056.8

[51] Int. Cl.$^6$ ........................................... C08J 9/00
[52] U.S. Cl. .................. 521/53; 521/56; 521/149; 521/150
[58] Field of Search .................. 521/149, 53, 56

[56] References Cited

U.S. PATENT DOCUMENTS

| | | | |
|---|---|---|---|
| 4,295,987 | 10/1981 | Parks | 525/366 |
| 5,264,495 | 11/1993 | Irie et al. | 521/149 |
| 5,462,972 | 10/1995 | Smith et al. | 521/149 |

*Primary Examiner*—Morton Foelak
*Attorney, Agent, or Firm*—Oblon, Spivak, McClelland, Maier & Neustadt, P.C.

[57] ABSTRACT

The present invention relates to powdery, insoluble, water-swellable, cross-linked polymers absorbing water, aqueous or serous liquids, which are formed of a) 55–99.9%-wt. polymerized unsaturated, polymerizable acid-groups—comprising monomers which are neutralized to the extent of at least 25 mol-%, b) 0–40%-wt. polymerized unsaturated monomers which are co-polymerizable with a), c) 0.1–5.0%-wt. of a cross-linking agent, and d) 0–30%-wt. of a water-soluble polymer, with the weight amounts of a) to d) being relative to anhydrous polymer, and the polymer powder is heated with an at least bifunctional compound reactive with acid groups to a temperature of 150° C.–250° C. under cross-linkage of the surface, and the polymer powder that is thus already surface-cross-linked is subjected to a repeated surface-cross-linking treatment using an at least bifunctional compound reactive with acid groups at a temperature of 150° to 250° C.

The present invention further relates to a process for the production of these polymers and to their use as absorbents for water and aqueous liquids, in particular in constructions for the absorption of body fluids, and in current-conducting or light-transmitting cables, as component in packing materials, as soil improver, and as artificial soil for plant breeding.

17 Claims, No Drawings

POWDERY POLYMERS CAPABLE OF ABSORBING AQUEOUS LIQUIDS, A PROCESS FOR THEIR PRODUCTION AND THEIR USE AS ABSORBENTS

The present invention relates to powdery, cross-linked polymers absorbing water and aqueous liquids, referred to as superabsorbers, having improved swelling properties and an improved retention capacity for aqueous liquids. The present invention further relates to a process for the manufacture of these polymers and to their use in absorbent sanitary articles and in technical fields.

Superabsorbers are water-insoluble, cross-linked polymers which, under swelling and formation of hydrogels, are capable of absorbing large amounts of body fluids, such as urine or blood, or other aqueous liquids and of retaining the absorbed liquid amount under a certain pressure. Owing to said characteristic absorption properties the polymers are mainly used in sanitary articles, for example, diapers and sanitary napkins.

The superabsorbers commercially available today are cross-linked polyacrylic acids or cross-linked starch-acrylic-acid-graft-polymers partially neutralized with sodium hydroxide solution or potassium hydroxide solution. In principle, powdery superabsorbers are manufactured by two methods:

According to the first method, partially neutralized acrylic acid in aqueous solution in the presence of a multifunctional cross-linking agent is converted into a gel by radical polymerization, the gel is then crumbled, dried, ground, and screened out to the desired particle size. The polymerization in solution may either be carried out continuously or discontinuously. Patent literature gives a wide spectrum of alternatives with respect to ratios of concentration, temperatures, kind and amount of cross-linking agents and initiators. Typical methods are described, for example, in U.S. Pat. No. 4,286,082, DE 27 06 135 and U.S. Pat. No. 4,076,633.

The second method includes the inverse suspension and emulsion polymerization. In these processes, an aqueous, partially neutralized acrylic acid solution is dispersed in a hydrophobic organic solvent by means of protective colloids or emulsifiers, and the polymerization is started by radical initiators. After completion of the polymerization, the water is azeotropically removed from the reaction mixture and the polymeric product filtered off and dried. The cross-linking reaction may be effected by incorporating a polyfunctional cross-linking agent, which is dissolved in the monomer solution, by polymerization, and/or by reacting suitable cross-linking agents with functional groups of the polymer during one of the production steps. The principle is described, for example, in U.S. Pat. No. 4,340,706, DE 37 13 601 and DE 28 40 010.

Initially, only the very high swelling capacity on contact of the absorber with the liquid, also referred to as free swelling capacity, had been the main factor in the development of superabsorbers; later it turned out, however, that not only the amount of absorbed liquid is of importance but also the stability of the swollen gel. However, absorbency, also referred to as swellability or free swelling capacity, on the one hand, and gel strength on the other hand, represent contrary properties, as is known by U.S. Pat. No. 3,247,171 and U.S. Pat. No. Re. 32,649. This means that polymers having a particularly high absorbency exhibit a poor strength of the swollen gel so that the gel is deformable under an exerted pressure when loaded by the body weight and further liquid distribution and liquid absorption is prevented at the same time. According to U.S. Pat. No. Re. 32,649 a balanced relation of the properties of these superabsorbers in a diaper construction between liquid absorption, liquid transport and dryness of the diaper on the skin is to be ensured. In this connection, not only is the polymer's capability of retaining a liquid under subsequent pressure, after swelling freely first, of importance, but also the fact that liquids are absorbed even against a simultaneously acting pressure, i.e., during the liquid absorption. This is the case in practice when a person sits or lies on a sanitary article or when shear forces are acting, e.g., by movements of legs. This specific absorption property is referred to, for instance according to EP 0 339 461 A, as absorption under load (AUL).

To provide superabsorbing polymers having the required property combination, i.e., high retention capacity, high gel strength and high absorbency under load, it is—as is known—necessary to treat the powdery polymers in a subsequent step.

In EP 0 083 022 B1, DE-OS 33 14 019 and DE 35 23 617 A1 a surface-cross-linking treatment of the polymers with compounds having at least two functional groups reactive with carboxyl groups is described, with polyols being particularly mentioned.

According to DE 40 20 780 C1 an improved swelling capacity under load of a superabsorbing polymer is achieved by heating the polymer powder with an alkylene carbonate which is applied, optionally diluted with water and/or alcohol.

However, the secondary treatment of water-swellable powdery polymers with compounds capable of reacting with more than one functional group of the polymer automatically results in a decrease of the swelling capacity. According to EP 0 089 022 B1 and EP 0 450 923 A, the reduction in the swelling capacity owing to the secondary treatment will become particularly high, when too much secondary treatment agent is chosen.

Thus, the decrease in the swelling capacity or in the retention results automatically, since the secondary treatment causes an additional cross-linkage of the water-swellable polymer particles.

According to the state of the art given in DE 40 20 780 C1, EP 0 450 924 A and EP 0 339 461 A, water-swellable resins are obtained and used by the secondary treatment of water-swellable, particulate polymers; these resins have an improved swelling capacity under load and their retention decreases with increasing cross-linking density and increasing pressure load, e.g., at an increase from 20 g/cm$^2$ to 60 g/cm$^2$, it decreases from 26 g/g to 8 g/g. These facts are summarized in Table 1, under consideration of the layer concentration. In this connection, layer concentration means the amount of superabsorbing polymer (mg) per surface unit of the absorber article (cm$^2$).

To meet the increasing trend of reducing the size and thickness of sanitary articles for esthetic reasons and in view of environmental and ecological aspects, it is possible, for instance, to reduce the large-volume fluff pulp portion in diapers and to increase the portion of superabsorber at the same time. In this case, however, the superabsorber has to take over additional functions with respect to liquid absorption and transport thereof, which were previously performed by the fluff pulp.

TABLE 1

| | Treatment agent | | Teabag Retention | Absorption under a load of | | | | |
|---|---|---|---|---|---|---|---|---|
| | Kind | Amount % | g/g | 0 | 14 | 20 | 40 | 60 g/cm² |
| | | | | g/g | | | | |
| DE 40 20 780 | | | | Layer concentration: 31.6 mg/cm² | | | | |
| Powder A Example | — | — | 45[1] | | | 6[2] | | |
| 9 | EC[4] | 0.5 | 43 | | | 28 | | |
| 10 | EC | 1.0 | 41 | | | 32 | | |
| 11 | EC | 1.5 | 40 | | | 34 | | |
| 12 | EC | 2.0 | 37 | | | 34 | | |
| 13 | EC | 2.5 | 32 | | | 32 | | |
| EP A 04 50 924 | | | | Layer concentration: 5.2 mg/cm² | | | | |
| Powder A 1 | — | — | 54[2] | | 10[3] | | | |
| Example 1 | GL[5] | 0.75 | 42 | | 25 | | | |
| Powder A 2 | — | — | 62 | | 9.5 | | | |
| Example 3 | GL | 1.0 | 43 | | 29 | | | |
| EP A 03 39 461 | | | | Layer concentration: 31.6 mg/cm² | | | | |
| Tab. 3 Example 1 | | no data | | 42 | 26[2] | | 13 | 8 |

[1] centrifuged 30 min. 0.9% NaCl
[2] 60 min. 0.9% NaCl
[3] 30 min. synth. urine 1 psi = 6.895 · 10³ Pa
[4] ethylene carbonate
[5] glycerol However, the use of conventional superabsorbers in diapers with portions of the superabsorber amounting to 40 or 60%-wt. involves considerable disadvantages which drastically limit the use of commercially available products. The known phenomenon of "gel blocking" caused by coagulated gel and the resulting reduction in the absorption rate and amount, in particular under increased load, must be considered as the cause for this. Accordingly, there was the object to provide polymers which, when used as superabsorbers in diaper constructions or other technical applications with increased polymer portions have a high swelling capacity under load at increased layer concentration.

It was found that water-swellable polymers having a high retention, increased swelling capacity under a load of more than 20 g/cm² as well as a high swelling capacity under load at increased layer concentration are obtained, when powdery, water-insoluble, cross-linked polymers capable of absorbing aqueous or serous liquids, such as blood, which polymers are formed of a) 55–99.9%-wt. polymerized unsaturated, polymerizable acid-groups-comprising monomers which are neutralized to the extent of at least 25 mol-%, b) 0–40%-wt. polymerized unsaturated monomers which are co-polymerizable with a), c) 0.1–5.0%-wt. of a cross-linking agent, and d) 0–30%-wt. of a water-soluble polymer, with the weight amounts of a) to d) being relative to anhydrous polymer, and which have been subjected to a surface-cross-linking treatment with a compound reactive with at least two functional groups of the polymers, preferably acid groups, at 150° C.–250° C., are once more subjected to a surface-cross-linking treatment using 0.1 to 5%-wt. of a compound reactive with at least two functional groups of the polymers in the presence of 0.1–5%-wt. of water, at temperatures of 150° C.–250° C. The preferred acid groups of the polymers are carboxyl groups.

In contrast to the observations that there is a deterioration in the absorption properties when the cross-linking density increases, the method according to the present invention involving the repetition of the surface-cross-linking treatment provides polymers which—most surprisingly—have an improved swellability both under increased load and at increased layer concentration.

The water-absorbing polymer to be used according to the present invention is obtained by polymerizing 55–99.9%-wt. of monomers having acid groups, e.g., of acrylic acid, methacrylic acid, 2-acrylamido-2-methylpropane sulfonic acid, or of mixtures of said monomers; the acid groups of the monomers are neutralized to the extent of at least 25 mol-% and are present, e.g. as sodium, potassium or ammonium salts. The neutralization degree preferably amounts to about at least 50 mol-%. Particularly preferred is a polymer formed of cross-linked acrylic acid or methacrylic acid which is neutralized to the extent of 50–80 mol-%.

Further monomers suitable for the production of the water-absorbing polymers include 0 to 40%-wt. acrylamide, methacrylamide, hydroxyethyl acrylate, dimethylaminoalkyl(meth)acrylate, dimethylaminopropyl acrylamide, or acrylamidopropyl trimethylammonium chloride. Percentages above 40% of these monomers will deteriorate the swell capacity of the polymers.

As cross-linking agent any compound may be used which has at least two ethylenically unsaturated double-bonds or one ethylenically unsaturated double-bond and one functional group reactive towards acid groups. Examples thereof include: acrylates and methacrylates of polyols, such as butanediol diacrylate, hexanediol dimethacrylate, polyglycol diacrylate, trimethylolpropane triacrylate, or allyl acrylate, diallyl acrylamide, triallyl amine, diallyl ether, methylenebisacrylamide or N-methylolacrylamide.

0 to 30%-wt. partially or completely saponified polyvinyl alcohol, polyvinyl pyrrolidone, starch or starch derivatives, polyglycols, or polyacrylic acids may be comprised as water-soluble polymers in the water-absorbing polymer. The molecular weight of said polymers is not critical provided that they are water-soluble. Preferred water-soluble polymers are starch, polyvinyl alcohol or mixtures of these polymers. The preferred content of these water-soluble polymers in the water-absorbing polymer amounts to about 1–5%-wt., in particular when starch and/or polyvinyl alcohol are present as soluble polymers. The water-soluble polymers may be present as graft polymers having the acid-groups-containing polymers.

In addition to polymers obtained by cross-linking polymerization of partially neutralized acrylic acid, those are preferably used which additionally comprise portions of graftpolymerized starch or of polyvinyl alcohol.

There are no specific limitations with respect to the particle shape of the absorber-polymer used. The polymer may be in the form of small beads obtained by inverse suspension polymerization, or of irregularly shaped particles obtained by drying and pulverizing the gel mass orginiating from the solvent polymerization. Usually, the particle size is in the range of between 20 and 2,000 µm, preferably between 50 and 850 µm.

The thermal treatment necessary for the surface-cross-linking treatment under reaction of the polyfunctional groups of a compound with the powdery polymer is carried out at temperatures of 150°–250° C., preferably of 170°–200° C. The suitable temperature depends on the kind of treating agent and on the residence time of the reaction components at the chosen reaction conditions.

At a temperature of 150° C., the thermal treatment must be carried out for several hours, whereas at 250° C. a few minutes—e.g., 0.5 to 5 minutes—are sufficient to obtain the desired properties. The surface-cross-linking thermal treatment may be carried out in conventional dryers or ovens, for example, rotary kilns, paddle dryers, disk dryers, or infrared dryers.

The surface-cross-linking treatment which is to be repeated according to the present invention may either be carried out under the same conditions as the first surface-cross-linkage or under modified conditions.

Accordingly, in the first surface-cross-linking treatment and in the repeated treatment according to the present invention, the same or different compounds may be used as at least bifunctional compounds reactive with acid groups. Polyols, polyamines, alkylene carbonates, alone or in admixture are used as these reactive, surface-cross-linking compounds, with ethylene carbonate, glycerol, dimethylpropionic acid, polyethylene glycol and triethanolamine being preferred. The compounds used for the surface-cross-linkage may be used in the form of aqueous solutions.

The agents according to the present invention have the property of absorbing large amounts of menstrual blood, urine or other body fluids rapidly and, for this reason, they are particularly suitable for the use in diapers, sanitary napkins, and incontinence articles or in articles for wound dressing.

The polymers which are post-treated twice according to the present invention are used in absorbent articles for various kinds of application, e.g., by mixing with paper, fluff pulp or synthetic fibers, or distributing the agent between substrates made of paper, fluff pulp or non-woven textiles, or by shaping in carriers to form a web.

The absorptivity and absorption rate of the polymers according to the present invention under a simultaneously acting compression load is considerably improved as compared to the starting products. Since the agents according to the present invention retain the absorbed liquids even under pressure, they are particularly easy to use. They are particularly suitable for the use in concentrations that—relative to hydrophilic fiber material, such as fluff pulp—are higher than those possible to date, i.e., at a reduced fluff pulp portion, and they have excellent absorption properties in constructions comprising 98–20%-wt. hydrophilic fibers and 2–80%-wt., preferably 15–70%-wt., and most preferably 25–60%-wt., of the absorbing resin.

The superabsorbers obtained according to the described processes surprisingly exhibit a considerable improvement in the absorption capacity of liquids under load, with a high gel strength and high retentions achieved at the same time. In particular, an extremely high initial liquid absorption rate under load is achieved so that 80% of the total capacity are achieved after only 15 minutes.

At retention values of more than 34 g/g the polymers according to the present invention have a swelling capacity of more than 22 g/g for a 0.9% NaCl-solution at a load of 40 g/cm$^2$. At a load of 60 g/cm$^2$ more than 18 g/g of 0.9% NaCl-solution are absorbed. As compared to polymers according to the art the differences will become evident. When the surface load is doubled and the pressure amounts to 40 g/cm$^2$, the polymers described in EP 0 339 461 A have a swelling capacity of 9 g of 0.9% NaCl-solution per gram, whereas the polymers according to the present invention absorb more than 18 g/g.

In a practical test for determining the absorptivity of polymers under load the superabsorbers according to the present invention show an improved suction power at an increased load.

With a high swelling capacity or retention, respectively, the polymers according to the present invention have a considerably higher swelling pressure than known superabsorbers.

Additionally, the polymers according to the present invention are useful as absorbent component for water or aqueous liquids in current-conducting or light-transmitting cables, as component in packaging materials, as soil improvers and as artificial soil for plant breeding.

TEST METHODS

To characterize the water-absorbing polymers, the retention (TB) and the absorption under load (AUL) for 0.9% NaCl-solution were measured and the swelling pressure was determined.

a) The retention is determined according to the tea bag test method and reported as average value of three measurements. Approximately 200 mg polymer are enclosed in a tea bag and immersed in 0.9% NaCl-solution for 20 minutes. Then the tea bag is centrifuged in a centrifuge (diameter: 23 cm; rpm: 1,400) for 5 minutes and weighed. One tea bag without water-absorbing polymer is used as blank.

$$\text{Retention} = \frac{\text{Weight} - \text{Blank reading}}{\text{Initial weight}} \, g/g$$

b) The absorption of 0.9% NaCl-solution under load (pressure load: 20, 40, 60 g/cm$^2$) is determined according to the method described in EP 0 339 461 A, page 7:

The initial weight of superabsorber is placed in a cylinder with sieve bottom, the powder is loaded by a piston exerting a pressure of 20, 40 and 60 g/cm$^2$, respectively. The cylinder is subsequently placed on a Demand-Absorbency-Tester (DAT) and the superabsorber is allowed to absorb 0.9% NaCl-solution for one hour. This test is repeated using the double and triple initial weight amount of superabsorber at a load of 40 g/cm$^2$.

c) The determination of the swelling pressure is carried out by means of the Stevens L.F.R.A. Texture Analyser, C. Stevens & Son Ltd., Laboratory Division, St. Albans AL1 1 Ex Hertfordshire, England.

The cylindrical glass measuring instrument forming part of the apparatus has a height of 3.5 cm and a diameter of 2.5 cm. Accordingly, the circular surface of the cylinder amounts to 4.91 cm$^2$.

0.500 g superabsorber of size fraction 20–50 mesh are weighed into the measuring cylinder having a diameter of 2.7 cm, and 10 ml of 0.9% NaCl-solution are added. Then the measuring cylinder is brought up by means of a lifting stage until the distance between the lower edge of the cylindrical measuring instrument and the surface of the sample in the measuring cylinder amounts to 12 mm. Through the expansion of the gel, the measuring cylinder is pressed upwards against a two-way load-sensing cell and the load is indicated at the device in grams.

d) To determine absorbency of the polymers from a matrix, a round fluff pad having a diameter of 6 cm and a weight of 2 g is soaked, lying in a Petri dish, with different amounts of 0.9% NaCl-solution. 0.20 g polymers are weighed into a cylinder of plexiglass having an inside diameter of 25.8 mm and a sieve fabric at the bottom (mesh width 36 μm) and loaded with a punch having a weight of 106 g and a diameter of 25 mm. The cylinder group (cylinder, polymer, punch) is weighed (A) and placed in the center of the moist pad. After one hour, the cylinder group is reweighed (B).

$$\text{Absorbency} = \frac{B - A}{0.20} \; g/g$$

EXAMPLES

Comparative Polymer A

A polyacrylic acid obtained by polymerization in solution, cross-linked with triallylamine and present as sodium salt neutralized to the extent of 70 mol-% was screened out to 90 to 850 μm after drying and grinding and was post-treated according to DE 40 20 780 with 1%-wt. of a 50% ethylene carbonate solution. The characteristic values are listed in Tables 2 and 3.

TABLE 2

| Retention (g/g) | Absorption under load (AUL) | | | Swelling pressure (g) |
| --- | --- | --- | --- | --- |
| | 20 g/cm$^2$ (g/g) | 40 g/cm$^2$ (g/g) | 60 g/cm$^2$ (g/g) | |
| 39.5 | 28.0 | 16.0 | 9.5 | 440 |

TABLE 3

Absorption in dependence on the layer concentration

| layer conc. (mg/cm$^2$) | 31.6 | 63.2 | 94.7 |
| --- | --- | --- | --- |
| absorption under load (AUL) (g/g) at 40 (g/cm$^2$) | 16.0 | 8.2 | 6.0 |

Example 1

Comparative polymer A is continuously fed into a paddle mixer at 1,000 kg/h and mixed with 1%-wt. of a 50% ethylene carbonate solution. The treatment solution is added in a finely divided manner by means of a two-component nozzle in the mixer.

For the thermal treatment, 90 kg/h of the mixture are continuously dosed into a dryer equipped with disk-shaped rotating mixing elements which are heated by vapor of 185° C. Subsequently, the mixture is cooled with air in the fluidized bed. The characteristic values are listed in Tables 4 and 5.

TABLE 4

| Retention (g/g) | Absorption under load (AUL) | | | Swelling pressure (g) |
| --- | --- | --- | --- | --- |
| | 20 g/cm$^2$ (g/g) | 40 g/cm$^2$ (g/g) | 60 g/cm$^2$ (g/g) | |
| 35.5 | 33.0 | 25.0 | 20.5 | 770 |

TABLE 5

Absorption in dependence on the layer concentration

| layer conc. (mg/cm$^2$) | 31.6 | 63.2 | 94.7 |
| --- | --- | --- | --- |
| absorption under load (AUL) (g/g) at 40 (g/cm$^2$) | 25.0 | 20.5 | 16 |

Example 2

By means of a two-component nozzle as in Example 1, 1000 kg of comparative polymer A are continuously mixed with a solution consisting of 2 kg glycerol, 10 kg water, and 12 kg ethanol and intermediately ensilaged.

80 kg of the polymer powder subjected to a surface-cross-linking treatment are continuously and hourly dosed into a paddle mixer heated by vapor of 180° C. and equipped with sickle-shaped mixing elements, and, after a mean residence time of about 30 minutes, cooled in a cold conveying screw. The test data of the powdery polymer are listed in Tables 6, 7 and 8.

TABLE 6

| Retention (g/g) | Absorption under load (AUL) | | | Swelling pressure (g) |
| --- | --- | --- | --- | --- |
| | 20 g/cm$^2$ (g/g) | 40 g/cm$^2$ (g/g) | 60 g/cm$^2$ (g/g) | |
| 36.5 | 32 | 24 | 19 | 680 |

TABLE 7

Absorption under load in dependence on the layer concentration

| layer conc. (mg/cm$^2$) | 31.6 | 63.2 | 94.7 |
| --- | --- | --- | --- |
| absorption under load (AUL) (g/g) at 40 (g/cm$^2$) | 24.5 | 21 | 15 |

TABLE 8

Determination of the absorbency under load from a matrix

| Solution of sodium chloride in pad (g) | Polymer acc. to Example 2 | Comparative Polymer A |
| --- | --- | --- |
| | Amount of sodium chloride solution absorbed by the polymer (g/g) | |
| 30 | 29.0 | 23.0 |

TABLE 8-continued

Determination of the absorbency under load from a matrix

|  | Polymer acc. to Example 2 | Comparative Polymer A |
|---|---|---|
| 21 | 24.5 | 16.0 |
| 15 | 21.0 | 10.5 |
| 9 | 15.0 | 10.0 |

Comparative Polymer B

A polyacrylic acid obtained by polymerization in solution in the presence of 3%-wt. polyvinyl alcohol (relative to acrylic acid), cross-linked with trimethylolpropane triacrylate and present as sodium salt neutralized to the extent of 70 mol-% was screened to a particle size of 120 to 500 μm after drying and grinding.

The secondary treatment of the polymer powder coated with 1%-wt. of a 50% aqueous ethylene carbonate solution is carried out in a rotary tubular kiln, according to DE 40 20 780. The test data of the obtained powdery polymer are listed in Table 9.

TABLE 9

| | Absorption under load (AUL) | | | Swelling pressure (g) |
|---|---|---|---|---|
| Retention (g/g) | 20 g/cm$^2$ (g/g) | 40 g/cm$^2$ (g/g) | 60 g/cm$^2$ (g/g) | |
| 42 | 27 | 12.5 | 9.0 | 380 |

Example 3

Comparative polymer B is mixed dropwise in a high-speed mixer with 2%-wt. of a solution consisting of 5 parts of polyethylene glycol 300, 10 parts of water, and 5 parts of ethanol, and then heated for 60 minutes in a rotary tubular kiln pre-heated to 180° C. and provided with a vapor hood. After cooling and screening of 0.6% oversize, the powdery polymer has the following characteristics:

TABLE 10

| | Absorption under load (AUL) | | | Swelling pressure (g) |
|---|---|---|---|---|
| Retention (g/g) | 20 g/cm$^2$ (g/g) | 40 g/cm$^2$ (g/g) | 60 g/cm$^2$ (g/g) | |
| 36 | 30.5 | 22 | 18 | 650 |

We claim:

1. A powdery, insoluble, water-swellable, cross-linked polymer absorbing water, aqueous or serous liquids, which is formed of
   a) 55–99.9%-wt. polymerized unsaturated, polymerizable acid-groups-comprising monomers which are neutralized to the extent of at least 25 mol-%,
   b) 0–40%-wt. polymerized unsaturated monomers which are copolymerizable with a),
   c) 0.1–5.0%-wt. of a cross-linking agent, and
   d) 0–30%-wt. of a water-soluble polymer, with the weight amounts of a) to d) being relative to anhydrous polymer, and the polymer powder is heated with 0.1–5%-wt. of an at least bi-functional compound reactive with acid groups to a temperature of 150° C.–250° C. under cross-linkage of the surface, wherein the improvement comprising subjecting the polymer powder once more to the surface-cross-linking treatment with 0.1–5%-wt. of an at least bifunctional compound reactive with acid groups at a temperature of 150° C.–250° C.

2. The polymer according to claim 1 characterized in that it has a retention of at least 34 g of a 0.9% sodium chloride solution per g of resin, an absorption of at least 18 g, preferably at least 20 g of a 0.9% sodium chloride solution per g of resin under a pressure of 60 g/cm$^2$, and an absorption of at least 12 g of a 0.9% sodium chloride solution per g of resin at a layer concentration of more than 90 mg resin per cm$^2$, as well as a swelling pressure of at least 600 g.

3. The polymer according to claim 1 characterized in that it is formed of acrylic acid, methacrylic acid and/or 2-acrylamido-2-methylpropane sulfonic acid used as acid-group-containing monomers.

4. The polymer according to claim 1 characterized in that the acid-groups-containing monomers are neutralized to the extent of at least 50 mol-%.

5. The polymer according to claim 1 characterized in that it is formed of acrylic acid which is neutralized to the extent of 50–80 mol-%.

6. The polymer according to claim 1 characterized in that water-soluble polymers are used in concentrations of 1–5%-wt.

7. The polymer according to claim 1 characterized in that starch and/or polyvinyl alcohol are used as water-soluble polymers.

8. The polymer according to claim 1 characterized in that the acid groups of the polymer are carboxyl groups and that the repeated surface-cross-linking treatment is effected with the same cross-linking agent as in the first treatment step.

9. The polymer according to claim 1 characterized in that the acid groups of the polymer are carboxyl groups and that the repeated surface-cross-linking treatment is effected with a cross-linking agent which is different from that used in the first treatment step or with mixtures of these agents.

10. The polymer according to claim 1 characterized in that the surface-cross-linking agents are polyols, polyamines, alkylene carbonates.

11. The polymer according to claim 10 characterized in that the surface-cross-linking agents are ethylene carbonate, glycerol, dimethylolpropionic acid, polyethylene glycol, and triethanolamine and that the agents are optionally used in the form of aqueous solutions.

12. A process for the production of a powdery, water-insoluble, cross-linked polymer absorbing aqueous and serous liquids, which is formed of
   a) 55–99.9%-wt. polymerized unsaturated, polymerizable acid-groups-comprising monomers which are neutralized to the extent of at least 25 mol-%,
   b) 0–40%-wt. polymerized unsaturated monomers which are co-polymerizable with a),
   c) 0.1–5.0%-wt. of a cross-linking agent,
   d) 0–30%-wt. of a water-soluble polymer,
with the weight amounts of a) to d) being relative to anhydrous polymer, and the polymer powder is heated with an at least bifunctional compound reactive with acid groups to a temperature of 150° C.–250° C., characterized in that the polymer powder is once more subjected to the surface-cross-linking treatment with 0.1–5%-wt. of an at least bifunctional compound reactive with acid groups at a temperature of 150° C.–250° C.

13. An absorbent article, comprising the polymer of claim 1 and a carrier.

14. The absorbent article of claim 13, comprising hydrophilic fibers and 2–80% by weight of the polymer of claim 1, relative to the total weight.

15. The article of claim 13, wherein said carrier is paper, fluff pulp or synthetic fibers.

16. The article of claim 13, wherein said article is a current-conducting cable, a light-transmitting cable, a packaging material, a soil improver or an artificial soil.

17. The article of claim 13, wherein said article is a diaper, a sanitary napkin, an incontinence article or a wound dressing.

* * * * *